United States Patent [19]

Svoboda et al.

[11] Patent Number: 4,782,231

[45] Date of Patent: Nov. 1, 1988

[54] STANDARD COMPONENT $^{99m}$TC ELUTION GENERATOR AND METHOD

[75] Inventors: Kristian Svoboda; Frantisek Melichar, both of Prague; Zdenek Sebek, Klecany; Milan Tympl, Prague, all of Czechoslovakia

[73] Assignee: Ustav jaderneho vyzkumu, Rez u Prahy, Czechoslovakia

[21] Appl. No.: 735,878

[22] Filed: May 20, 1985

[30] Foreign Application Priority Data

May 18, 1984 [CS] Czechoslovakia ............ 3764-84

[51] Int. Cl.$^4$ ............................................. G21G 1/02
[52] U.S. Cl. ............................. 250/432 PD; 252/645; 422/159; 423/2; 376/186
[58] Field of Search ............ 250/432 PD, 303; 252/645; 422/159; 423/2; 376/186

[56] References Cited

U.S. PATENT DOCUMENTS

| | | | |
|---|---|---|---|
| 3,576,998 | 5/1971 | Deutsch | 250/432 PD |
| 3,774,035 | 11/1973 | Litt | 250/432 PD |
| 3,833,469 | 9/1974 | Robson | 250/303 |
| 4,206,358 | 6/1980 | Matthews et al. | 250/432 PD |
| 4,280,053 | 7/1981 | Evans et al. | 250/432 PD |
| 4,387,303 | 6/1983 | Benjamins | 250/432 PD |

OTHER PUBLICATIONS

McGraw-Hill Encyclopedia of Science & Technology, 5th ed., 1982, vol. 9, p. 128.
Manual of Radioisotope Production, International Atomic Energy Agency, 1966, pp. 103-106.

Primary Examiner—Craig E. Church
Assistant Examiner—Jack I. Berman
Attorney, Agent, or Firm—Klein & Vibber

[57] ABSTRACT

This invention relates to a standard component $^{99m}$TC elution generator useful for medical purposes and consisting of prefabricated component parts. The main generator column of the device may be used both as an irradiation container and an elution container, enabling the user to supply activated or nonactivated parts. The main generator column made from by neutrons little activable materials serves first as reactor irradiation ampoule and after having been activated in the reactor by neutrons and after a simple adjustment serves directly as the generator column. It is filled with water insoluable molybdates or polymolybdates (with the molybdenum content in the range 10-40%), easily releasing $^{99m}$Tc generated by radioactive decay of the mother $^{99}$Mo formed in it by neutron activation. This column filling serves originally as target material for reactor irradiations and afterwards it is directly used as the generator elution matrix. Accordingly, all components of the generator can be produced in a "ready-to-use" form and supplied as inactive material. When non-activated parts are used, activation is performed on-site by a local reactor. The use of nonactivated parts is advantageous because they are more easily and more safely manufactured and transported. The invention further provides for efficient generation of $^{99m}$Tc radionuclides from medium neutron flux irradiation of molybdenum in a natural isotopic mixture.

6 Claims, 1 Drawing Sheet

U.S. Patent
Nov. 1, 1988
4,782,231
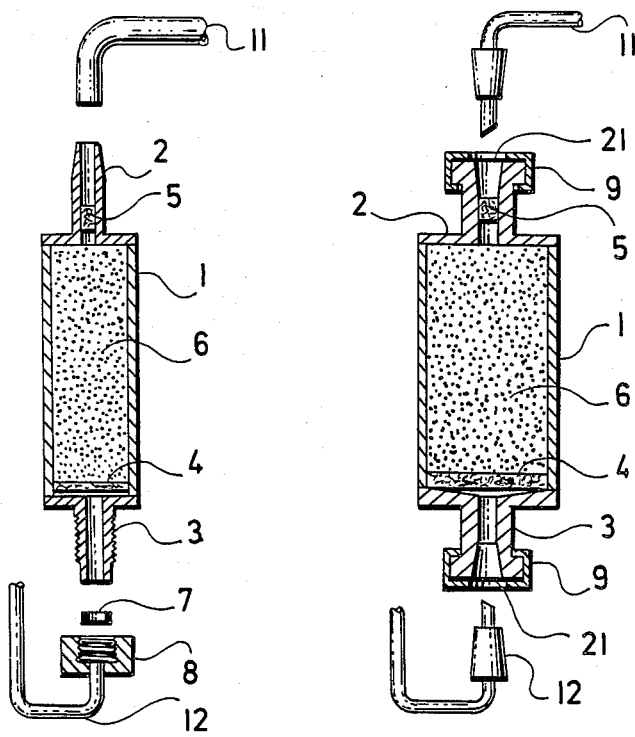
FIG. 1
FIG. 2
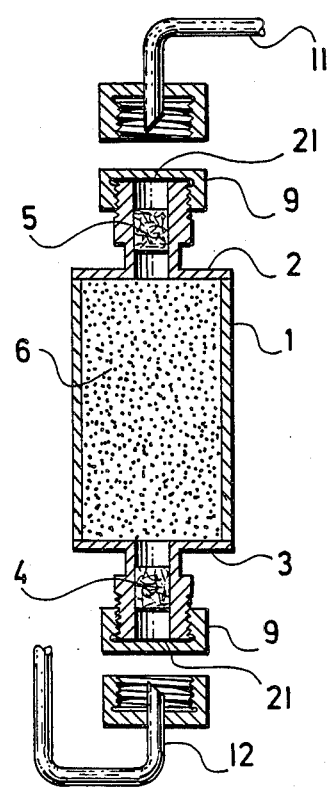
FIG. 3
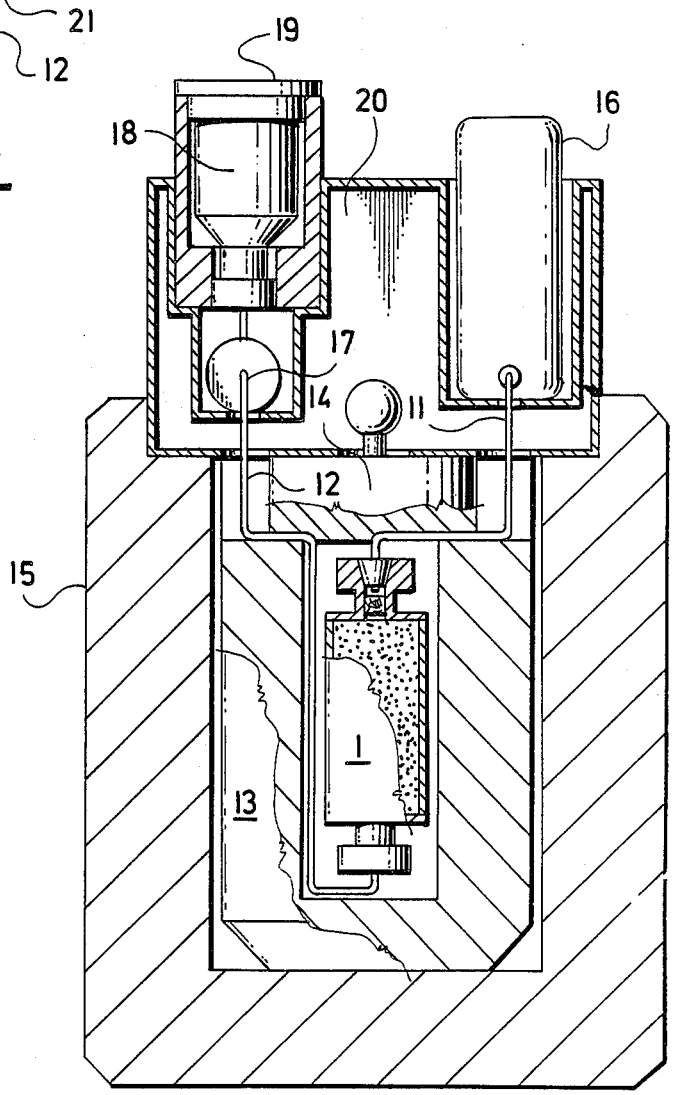
FIG. 4

STANDARD COMPONENT $^{99m}$TC ELUTION GENERATOR AND METHOD

This invention relates to a standard component $^{99m}$Tc elution generator useful for medical purposes and consisting of prefabricated component parts. The fundamental part of the generator is formed by the main generator-ampoule-column made from materials with low radioactivation ability by neutrons. It serves first as the reactor irradiation ampoule and after suitable adjustment directly as proper generator column. The ampoule-column is filled with the target material—elution matrix, that contains high amounts of molybdenum (up to 40% by weight) consisting of water insoluable molybdates or polymolybdates releasing easily $^{99m}$Tc technetium generated in the column by radioactive decay of mother $^{99}$Mo, formed in the matrix structure by neutron activation. The filling of the ampoule-column serves originally as target material for reactor irradiations and afterwards it is directly used as the proper elution matrix of the generator. The high content of molybdenum in the target material-elution matrix makes possible the utilization even of low to medium power reactors for neutron activation. The production possibility of the main generator column as completely inactive material already before the reactor irradiation facilitates substantially the post-irradiation assembly procedure. In such a way the manufacturer can supply not only the complementary components but even the main generator ampoule-column as inactive parts, that can be produced highly effective in large batches and kept for a long time on stock.

BACKGROUND OF THE INVENTION $^{99m}$Tc is a widely used radionuclide in radiopharmaceutical and nuclear medicine applications. The particular medical advantage of this radionuclide is its very short half-life of about 6 hours. However, the short half-life creates manufacture and delivery problems, because the radionuclide must be used very soon after it is produced. For this reason, $^{99m}$Tc is preferably supplied to hospitals on demand by an on-site generator, through disintegration of isotopic molybdenum ($^{99}$Mo) and chemical separation of the $^{99m}$Tc product. High purity and high activity are important, so that the $^{99m}$Tc product may be used immediately as a pertechnate, in the preparation of radionuclide tracer compounds, etc.

Current medical technology requires the use of radionuclide generators which can supply radioactive levels of at least 4 GBq, most often 8–12 GBq, and in some cases as high as 40 GBq per generator. Of radionuclide the generators now in use, elution generators are the most advantageous because they provide for rapid, efficient, and simple production of the desired radionuclides. However, in practice, most elution generators rely on aluminum oxide as a sorption material, which has a sorption capacity of only several percent by weight of molybdenum. This limits the activity of the generator to only several hundred MBq when natural isotopes of molybdenum are irradiated by a medium neutron flux ranging approximately between $10^{17}$ and $10^{18}$ n/m$^2$s. This level of activity is insufficient for medical applications. Known elution generators must therefore rely on either (a) the irradiation of enriched $^{98}$Mo as a target material for a high-intensity neutron flux; or (b) a carrier-free $^{99}$Mo isotope obtained by fission of uranium. These known devices and processes require a large capital investment; high energy and labor costs; a complex series of processing and purification steps involving highly radioactive components; the separation of $^{99}$Mo from uranium fission products, which are about twenty times more active than the useable radionuclide.

Thus, for many applications the advantages of known elution generators have been outweighed by the practical and economic disadvantages, and other types of generators have been sought. Methods of $^{99m}$Tc production allowing its separation from low specific activity parent $^{99}$Mo are to be used. For example, a sublimation of $^{99m}$Tc may be obtained from a suitable $^{99}$Mo compound. Or, $^{99m}$Tc products may be extracted from a strongly alkaline aqueous solution of a molybdate of $^{99}$Mo by methylethylketone. These processes permit the production of $^{99m}$Tc products of medically sufficient activity from low to medium neutron flux irradiation within the range of about $5\times10^{16}$ to $5\times10^{17}$ n/m$^2$s. However, these chemical methods are substantially more complex, time-consuming, and labor intensive than a common elution generator. They may not be economically and conveniently practiced within a self-contained on-site apparatus. Instead, a centralized manufacturing and processing center will generally supply technetium 99m produced by sublimation or extraction to local hospitals and clinics. Although miniaturized extraction and sublimation generators are available for on-site hospital use, they remain complex and expensive.

The technology of known $^{99m}$Tc generators is discussed in R. E. Boyd, *Recent Developments in Generators of $^{99m}$Tc Radiopharmaceutical and Labeled Compounds*, IAEA (Vienna: 1973), p. 1–26; R. E. Boyd, *Technicium 99m Generators—The Available Options*, Int. J. Appl. Rad. & Isot. (New York: 1982), Vol. 33, p. 801–2; and V. J. Molinsku, *A Review of $^{99m}$Tc Generator Technology*, Int. J. Appl. Rad. & Isot. (New York: 1982), Vol. 33, p. 811–19.

Other practitioners have sought to improve elution generators by replacing the aluminum oxide sorption material with a sorption matrix. The matrix is intended to recover greater amounts of molybdenum from which $^{99m}$Tc can be eluated, thus improving efficiency and yield. J. V. Evans, P. W. Moore, M. S. Shying, & J. M. Soddeau, "A New Generator For $^{99m}$Tc," *Third World Congress on Nuclear Medicine and Biology*, pp. 1592–5 (Paris: 1982). The Evans device uses a sorption matrix of zirconium molybdate obtained from irradiated molybdenum oxide that is dissolved in a lye solution, precipitated by zirconium nitrate, and dried at 105° C. The approximate chemical composition of this sorption material is $ZrO_2 \cdot MoO_3 \cdot xH_2O$, having a molybdenum concentration of approximately 25% by weight. Through a hydration and shaping process, the material achieves elution of $^{99m}$Tc from $^{99}$Mo with an efficiency of 70–90%.

In experiments performed by the inventors in addition to zirconium molybdate also with titanium molybdate and polymolybdates of both elements containing 10–40% by weight molybdenum (with preferred content 20–30%) elution efficiencies 40–80% have been achieved. In contrary to previous authors (Evans et al) the elution matric was not made from already previously irradiated radioactive material dried at 105° followed by hydration but in our case the elution matrix has been made from completely inactive material and dried at lower temperatures, prior to its activation by neutrons in the reactor. The drying has been performed at 40°-50° C., lasting many hours, in some cases even drying at room temperature (approximately. 20° C.), lasting many days, has been used. The grain size of the matrix material usually has been in the range 50-140 /um. The inactive matrix prepared in such a way has been directly used as target material for the exposure to neutron activation in the reactor prior to elution.

SUMMARY OF THE INVENTION

It is an object of the invention to overcome or minimize a number of disadvantages of known $^{99m}$Tc devices. These disadvantages include: (a) the limited availability of enriched $^{98}$Mo and of reactors with a high neutron flow; (b) the practical and economic difficulties inherent in elution devices based on $^{99}$Mo obtained from fission products; (c) MAAE control and disposal of used fission material and fission byproducts; (d) the risk of radioactive contamination; (e) the complexity and cost of sublimation and extraction processes and devices; (f) transport and delivery problems involving $^{99m}$Tc products, activated generators, and fully assembled generators; (g) reliance on a neutron flow exceeding $10^{18}$ n/m$^2$s to achieve elution generator activity above 2 GBq from n, gamma reaction with $^{99}$Mo; and (h) the need for special sterilization procedures.

According to the invention, these problems are alleviated or eliminated by an elution generator made of independent component parts. The major component is a main column which serves first as an irradiation ampoule for activation of the target material, and then is adjusted for immediate use as an elution column containing the activated material serving directly as elution matrix.

The main column is preferably cylindrical and is provided with a supply means and a discharge means, such as tubes or hoses. It is composed of a corrosion-resistant material that is relatively inert with respect to neutrons, such as aluminum, zirconium, or quartz. The column is filled with target material containing at least 10% molybdenum by weight, so that efficent selective elution of $^{99m}$Tc from $^{99}$Mo will result. Powdered or granular molybdates are generally used, such as polymolybdates of zirconium and/or titanium. The particles are held within the column by a porous material that is relatively unaffected by neutrons, such as a porous sinter of silicon or zirconium oxide, graphite, felt, quartz, or an aluminum fiber composite. The porous material allows the elution solution to pass freely.

The main column can be hermetically sealed for radiation sterilization during activation by the neutron flow. Before exposure in the reactor, the ends of the column are hermetically sealed, such as by fusing, aluminum packing, or screw-type closures with aluminum packing. In addition, the entire column can be wrapped with aluminum foil to prevent bacterial contamination after removal from the reactor and to provide an aseptic connection with other components of the apparatus. After irradiation, the sealed ends of the column are breached and the supply and discharge tubes are attached in a sterile manner. The opposing ends of the supply and discharge tubes are sealed or plugged, so that the interior of the column is maintained in a sterile condition. The column, together with connecting means, is placed in a container for transportation to the user, preferably of lead or uranium deprived of $^{235}$U. The primary container is placed in another secondary protective container which is hermetically sealed.

The other components of the assembled device, also sterilized and protected against contamination, comprise a vessel containing an apyrogenous elution solution, preferably 0.9% NaCl by weight, in sterile connection with the supply tube; a protective column filled with a sorbent, preferably zirconium oxide or aluminum oxide, and connected to the discharge tube; a piercing head with a connecting hose from the discharge tube; and evacuated bottles for the eluate connected to the piercing head. The apparatus also comprises a laboratory screening container and a support base for the assembled components. The apparatus can be delivered assembled or unassembled. Unassembled delivery is preferable, because the main column can then be separately manufactured, processed, and delivered.

Table I shows the activity of the new elution generator at different column volumes and different neutron flows, when used with a target material containing 25% molybdenum by weight in a sorption matrix at a bulk weight of 1 g/ml. The activities are related to $^{99}$Mo and to a reference date 72 hours after a prior continuous irradiation for 90 hours.

TABLE I $^{99}$Mo ACTIVITY OF $^{99m}$Tc GENERATOR IN GBq
neutron flow is in n/m$^2$s;
volume is in ml; dimensions are in cm.

| VOL-UME | MAIN COLUMN HEIGHT W GIVEN DIAMETER | | | $^{99}$Mo ACTIVITY IN GBq AT GIVEN NEUTRON FLUX × $10^{17}$ | | | |
|---|---|---|---|---|---|---|---|
| ml | 1.0 cm | 1.5 cm | 2.0 cm | 5 × 10$^{-1}$ | 1 | 2 | 5 |
| 3 | 3.8 | 1.7 | — | 0.5 | 1 | 2.5 | 6.5 |
| 5 | 6.4 | 2.8 | — | 1 | 2 | 4 | 11 |
| 10 | 12.7 | 5.6 | 3.2 | 2 | 4 | 8 | 22 |
| 20 | — | 11.3 | 6.4 | 3.5 | 8 | 17 | 43 |
| 30 | — | — | 9.5 | 5 | 12 | 25 | 65 |

When the main column is made of zirconium, both it and the elution matrix are activated. Due to the 10:1 ratio of Zr to Mo by weight, and due to the activating cross sections, the irradiation time, and the lethal time, the main column exhibits $^{97}$Zr activity with a half-life of 17 hours, and which is not more than double the $^{99}$Mo activity at the time of irradiation. At the reference time of 72 hours, $^{97}$Zr activity is roughly 20% of the $^{99}$Mo activity. The column also exhibits a $^{95}$Zr activity having a half-life of 64 days in equilibrium with $^{95}$Nb having a half-life of 35 days, representing roughly 10% the activity of $^{99}$Mo after irradiation and 20% at the reference time. These conditions create no significant or substantial hazards or problems with respect to construction and screening of the generator.

When the main column is made of aluminum, the total radioactivity is lower, as only the target material is activated. The half-life of $^{28}$Al is 2.2 minutes, and therefore nuclear-clean aluminum creates no lingering radioactive byproducts from the neutron irradiation, and no column activity remains at the reference time.

Column contaminants can be activated by neutron irradiation, and in addition aluminum itself may become activated by fast neutrons via $^{27}$Al/n,alfa/$^{24}$Na reaction to natrium ($^{24}$Na). Natrium has a half-life of 15 hours. From an irradiation point of view the most preferable column material is quartz, where only very small amounts of $^{31}$Si (half-life=2.6 hours) are activated. Quartz is also chemically inert and is low in contaminants; but quartz columns tend to be fragile.

A neutron flux of $10^{16}$ n/m$^2$s corresponds to an irradiation dose of 360 kGy during one hour. All microorganisms and their latent forms are destroyed by irradiation at all doses exceeding 360 kGy. Thus, irradiation for more than one hour in a moderate neutron flow, as disclosed herein, serves the dual even purpose of target sorption material activation and reliable column sterilization.

BRIEF DESCRIPTION OF THE DRAWINGS

FIGS. 1-3 show three embodiments of the main generator column in longitudinal section.

FIG. 4 is an embodiment of the fully assembled apparatus in longitudinal section.

DETAILED DESCRIPTION

The invention is further described with reference to a number of examples. It will be understood by skilled practitioners that these examples are illustrative, and do not limit the scope of the invention or the appended claims.

EXAMPLE 1

With reference to FIG. 1, the main generator column 1 is cylindrical and has a ratio of diameter to height of 1:3-5. The main column 1 is made of zirconium or aluminum, and has an upper flange 2 and a lower flange 3 of the same material. Each flange is affixed to the column as shown, and each is welded shut at the end opposite the column, to form a hermetic seal. Upper flange 2 is provided with a narrower and slightly conical extension tube 22. The lower flange 3 is threaded and has an extension tube 23. The column is filled with a target material 6, such as zirconium molybdate dried at 50° C. and dispersed in particles ranging in size from 50 to 100 $\mu$m (270 to 140 mesh). The target material is sealed within the column by sinter 4, of porous aluminum or zirconium oxide, at the lower end of the main column 1 near flange 3; and by a plug 5 of quartz, aluminum composite, or graphite felt an the upper end of column 1 within flange 2.

Prior to irradiation, as discussed above, the entire main column assembly is wrapped in aluminum foil to prevent contamination, particularly of the flanges 2 and 3. After irradiation, the foil is removed from the column assembly under sterile conditions, and the welded ends of flanges 2 and 3 are opened by grinding or filing. The threaded lower flange 3 is then connected to a threaded end-piece 8 into which a seat 7 of silicon rubber is inserted. The end-piece 8 is connected to an L-shaped discharge tube 12. A supply tube 11 is affixed to flange 2.

EXAMPLE 2

FIG. 2 shows a cylindrical main column 1 made of aluminum or zirconium as in FIG. 1. The column 1 is provided at its lower end with a flange 3. The flange 3 is slightly conical at the interior, where it meets column 1, and contains a discharge tube 24 that terminates with a widened part and a conical internal opening 25. The flange 3 and discharge tube 24 are closed by cap 9 and aluminum foil 21 having no conical recess on the internal side. The column is filled with zirconium molybdate particles 6, which have been dried for several days at room temperature. The particles range in size from 10-150 $\mu$m (100-200 mesh). The lower end of column 1 is sealed by a porous sinter 4 of silicon dioxide. The upper end is sealed by plug 5 of graphite felt, beyond which is another cap 9 and foil 21. The column is irradiated according to the invention and is then transferred to a sterile environment. The caps 9 and foil 21 are treated with a disinfecting solution. The column 1 is then connected to sterile supply tube 11 and sterile discharge tube 12 at its opposite ends by piercing the foil 21 at each end, and firmly inserting the respective tube 11 or 12 to achieve a tight fit.

EXAMPLE 3

FIG. 3 shows a symmetrically closed embodiment. Main column 1 is aluminum or zirconium and has a diameter to height ratio of 1:2-5. Identical threaded flanges 2 and 3 are welded to column 1, flange 2 at the upper end and flange 3 at the lower end. Within each flange are tubes 27 closed by caps 9 packed internally with aluminum foil 21. Target material 6, such as titanium molybdate dried at 40° C. and having a particle size of 70-150 $\mu$m (100-200 mesh), is placed within the column. The target material is sealed within the column by plugs 5. After irradiation, caps 9 are removed in a sterile environment and supply tube 11 and discharge tube 12, each with an end-piece 8, are screwed in place.

EXAMPLE 4

FIG. 4 shows an assembled generator of the invention. The main column 1 with supply and discharge tubes 11 and 12, as described in Examples 1-3 and 6 and as shown in FIGS. 1-3, is placed within a primary transport container 13 made of lead or depleted uranium. The tubes 11 and 12 are placed within openings in the container 13 during transport, and their ends are aseptically sealed against bacterial contamination by plugs and/or wrapping. Container 13 has a cover 14 with a spherical handle 28 to facilitate manipulation of cover 14. The cover 14 is held securely in place by at least two screws, or by some other known method, such as rectangular hoops or friction clamps secured around the container 13. For transportation to the end user, these components are placed in a protective sheet container (not shown).

Upon arrival at the use-site, the column 1 and container 13 assembly are removed from the protective container and placed in a laboratory container 15. Lab container 15 is a thick-walled vessel made of lead or depleted uranium. The sealed outer end of supply tube 11 is broken and, without loss of sterility, is connected to vessel 16, which contains a sterile apyrogenous physiological solution. The sealed outer end of discharge tube 12 is broken and, without loss of sterility, is connected to protective column 17, which contains a sorbent, such as hydrated zirconium oxide. The protecting column 17 in turn is connected to the piercing head of evacuated, flanged, and sterilized penicillin-type bottles 18. The bottles 18 are situated in a thin-walled lead container 19. The components are placed within a cylindrical enclosure 20 that is provided with cavities to house them. Enclosure 20 itself fits within a circular recess of lab container 15.

Each elution is performed by placing an evacuated bottle 18 on the piercing head. In response, a corresponding volume of solution is sucked from vessel 16, passes in through supply tube 11, through main column 1, out through discharge tube 12, into column 17 and finally into bottle 18. The eluate, having passed through the sorption material 6, contains $^{99m}$Tc radionuclides when it reaches bottle 18. When elution is complete, the sterile seal is maintained by placing a non-evacuated bottle 18 over the piercing head.

EXAMPLE 5

In another embodiment of the invention, the elution generator may be supplied to the user in an assembled version, substantially as shown in FIG. 4. The main column 1 is stored in lab container 15 by the manufacturer and the entire device is shipped to the user. This embodiment requires a stronger connection between enclosure 20 and cover 14, such as a heavy threaded bar.

EXAMPLE 6

In its simplest embodiment, not illustrated, the main column can be made of a quartz tube narrowed conically at both extremities, containing target material (ie, zirconium molybdate particles 100–150 μm in size; dried at 60° C.), and fused closed. The target material is packed tightly in the narrow ends of the column by quartz wadding. Prior to irradiation, the sealed column is wrapped in aluminum foil. After irradiation, the narrow ends of the column are cut and broken close to each end by a vidium knife or a file. Bacterial infection is prevented by careful flaming of the ends. Supply and discharge hoses, preferably of silicon rubber, are affixed to the ends of the column. The column is shielded by a simple coiled lead sheet within a laboratorium arrangement and is connected to a vessel, such as a birette or a separating funnel, containing the elution solution.

In yet another embodiment, the quartz column can be used in a more complex apparatus as shown in Example 4.

In operation, the elution generator of the invention, comprising primarily the main generator column, can produce a standard $^{99m}$Tc elution of several GBq for a medium intensity neutron flux of 2 to $5 \times 10^{17}$ n/m²s. The columns of the invention are manufactured in a nonactivated state, which makes their manufacture much easier and safer. Later activation of the column also permits a single activation and sterilization step. The apparatus as a whole may be manufactured and delivered as components which are readily interconnected for use. In addition, the main column can be supplied separately, and through and independent delivery chain, whereby it may be activated by irradiation in a local reactor. This is a particularly important consideration in developing countries. Activation of the column itself and its contaminants (if any) is not a problem, nor is safe transport after irradiation, because the "extra" activity is always equal to or less than that of $^{99}$Mo.

The invention as a whole is advantageous because it permits the use of a reactor with a medium intensity neutron flux which are more readily available than these which provide the high intensity activation required by conventional generators; it benefits from a simple and elegant design in manufacture, delivery and use; it achieves simultaneous sterilization and activation of the main elution column; and it permits independent delivery of activated and nonactivated components.

We claim:

1. A method of preparation of $^{99m}$Tc elution comprising the steps of, filling a main column composed of a material selected from the group consisting of aluminum, zirconium, quartz, carbon and oxides thereof with a target material comprising at least 10% by weight of molybdenum;

plugging the ends of the main column with a porous material;

closing the ends of the main column;

wrapping the ends of the main column to protect against secondary bacterial contamination;

activating the target material to form a $^{99}$Mo containing sorption matrix accompanied simultaneously by radiation sterilization of the main generator column and its contents by exposure to neutron and accompanied gamma radiation in a reactor;

opening the ends of the main generator column in sterile environment under aseptic conditions of manipulation;

connecting a supply tube to one end of the main column and a discharge tube to the other end in a sterile manner;

placing the main column, supply tube, and discharge tube in a transport container composed of a material selected from the group consisting of lead or depleted uranium;

placing the transport container in a laboratory container, the laboratory container also housing an elution vessel, a protective column, and at least one eluate collection bottle;

connecting the supply tube to an elution vessel in a sterile manner, the elution vessel containing an elution solution;

connecting the discharge tube to one end of a protective column in a sterile manner, the other end having a piercing head;

piercing the seal of an evacuated eluate collection bottle with the piercing head;

drawing the eluation solution through the supply tube, main column containing the sorption matrix, discharge tube, and protective column, and into the eluate collection bottle, the eluate containing $^{99m}$Tc.

2. A method as in claim 1 wherein the ratio of the diameter of the main column to its height is 1:2–5; the target material is selected from the group consisting of molybdates and polymolybdates of titanium and zirconium having a molybdenum content of from 20 to 40% by weight; the porous plug is composed of a material selected from the group consisting of aluminum, zirconium, quartz, carbon, oxides and composites thereof, and felt, the elution solution is a 0.9% solution of NaCl by weight; the protective column contains a sorbent selected from the group consisting of zirconium oxide and aluminum oxide; and the transport container is a material selected from the group consisting of lead and depleted uranium.

3. A method as in claim 1 additionally comprising the steps of placing the transport container in a protective container; shipping the protective container to the user, and removing the transport container from the protective container prior to the step of placing the transport container in the laboratory container.

4. A method as in claim 2 additionally comprising the steps of placing the transport container in a protective container; shipping the protective container to the user, and removing the transport container from the protective container prior to the step of placing the transport container in the laboratory container.

5. A method as in claim 1, wherein the target material is selected from the group consisting of molybdates and polymolybdates of zirconium titanium and other elements, the specific activity thereof, expressed in Bq/g of the corresponding element 25 hours after reactor irradiation end, is lower than twice the specific activity of $^{99}$Mo reached irradiating under the same conditions molybdenum in its natural isotopic mixture; the content of molybdenum in the target plugs, covers and other parts of the main generator column are made from elements and their oxides, the specific activity thereof, 24 hours after reactor irradiation end, is lower than twice the specific activity of $^{99}$Mo reached by irradiating under the same conditions molybdenum in its natural isotopic abundance, the specific activity is evaluated by Bq/g of the corresponding element; wherein the elements used are selected from the group consisting of zirconium, titanium, aluminum, carbon, silicon and their oxides; the porous plugs are made from the above mentioned materials formed into fibers, composites, felt or wool.

6. A method as in claim 5 additionally comprising the steps of placing the transport container in a protective container; shipping the protective container to the user, and removing the transport container from the protective container prior to the step of placing the transport container in the laboratory container.

* * * * *